US00PP15696P2

(12) United States Plant Patent
Sakazaki

(10) Patent No.: US PP15,696 P2
(45) Date of Patent: Mar. 22, 2005

(54) *PETUNIA* PLANT NAMED 'USTUNI164'

(50) Latin Name: *Petunia×hybrida*
Varietal Denomination: USTUNI164

(75) Inventor: Ushio Sakazaki, Shiga (JP)

(73) Assignee: Plant 21 LLC, San Marcos, CA (US)

( * ) Notice: Subject to any disclaimer, the term of this patent is extended or adjusted under 35 U.S.C. 154(b) by 0 days.

(21) Appl. No.: 10/827,540

(22) Filed: Apr. 19, 2004

(51) Int. Cl.[7] ..... A01H 5/00
(52) U.S. Cl. ..... Plt./356
(58) Field of Search ..... Plt./356

(56) References Cited

U.S. PATENT DOCUMENTS

PP8,768 P * 6/1994 Hirabayashi et al. ..... Plt./356

OTHER PUBLICATIONS

UPOV ROM GTITM Computer Database, GTI Jouve Retrieval Software 2004/04 Citations for USTUNI164 and 'Revolution White'.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Petunia* plant named 'USTUNI164', characterized by its semi-upright to cascading plant habit; freely branching habit; numerous large single flowers that are white in color; and good garden performance.

1 Drawing Sheet

Botanical classification/cultivar designation: *Petunia×hybrida* cultivar USTUNI164.

BACKGROUND OF THE INVENTION

The present Invention relates to a new and distinct cultivar of *Petunia* plant, botanically known as *Petunia×hybrida,* and hereinafter referred to by the cultivar name USTUNI164.

The new *Petunia* is a product of a planned breeding program conducted by the Inventor in Hikone, Shiga, Japan. The objective of the breeding program is to create new disease-resistant and heat-tolerant *Petunias* with semi-upright plant habit and attractive flower colors.

The new *Petunia* originated from a cross-pollination made by the Inventor on May 6, 1998 of the *Petunia* cultivar Titan White, not patented, as the female, or seed parent, with an unnamed selection of *Petunia,* not patented, as the male, or pollen parent. The new *Petunia* was selected as a single plant from the resulting progeny on Jun. 15, 1999 in Gensingen, Germany, on the basis of its plant habit and attractive flower coloration.

Asexual reproduction of the new cultivar by terminal vegetative cuttings since Jun. 25, 1999, taken in Gensingen, Germany has shown that the unique features of this new *Petunia* are stable and reproduced true to type in successive generations.

SUMMARY OF THE INVENTION

Plants of the cultivar USTUNI164 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USTUNI164'. These characteristics in combination distinguish 'USTUNI164' as a new and distinct cultivar:

1. Semi-upright to cascading plant habit.
2. Freely branching habit.
3. Numerous large single flowers that are white in color.
4. Good garden performance.

In side-by-side comparisons conducted in Hikone, Shiga, Japan, plants of the new *Petunia* differed from plants of the female parent, the cultivar Titan White, in the following characteristics:

1. Plants of the new *Petunia* were more cascading than and not as upright as plants of the cultivar Titan White.
2. Plants of the new *Petunia* were more vigorous than plants of the cultivar Titan White.
3. Plants of the new *Petunia* were more rain-tolerant than plants of the cultivar Titan White In side-by-side comparisons conducted in Hikone, Shiga, Japan, plants of the new *Petunia* flowered earlier and had larger flowers than plants of the male parent selection.

Plants of the new *Petunia* can be compared to plants of the cultivars Surfinia White, not patented, and Cascadia Choice, U.S. Plant Pat. No. 8,768. In side-by-side comparisons conducted in Gensingen, Germany, plants of the new *Petunia* differed primarily from plants of the cultivars Surfinia White and Cascadia Choice in flower size as plants of the new *Petunia* have large flowers than plants of the cultivars Surfinia White and Cascadia Choice.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the bottom of the sheet comprises a side perspective view of a typical plant of 'USTUNI164' grown in a container.

The photograph at the top of the sheet is a close-up view of typical flowers and leaves of 'USTUNI164'.

DETAILED BOTANICAL DESCRIPTION

The aforementioned photographs and following observations and measurements describe plants grown in Bonsall, Calif., in an outdoor nursery during the early spring under full sun conditions with day temperatures ranging from about 18 to about 35° C. and night temperatures ranging from about 10 to about 21° C. After planting rooted cuttings, plants were grown for about eight weeks in 15-cm containers. Color references are made to The Royal Horticultural Society Colour Chart, 1995 Edition, except where general terms of ordinary dictionary significance are used.

Botanical classification: *Petunia×hybrida* cultivar USTUNI164.

Parentage:

*Female parent.*—*Petunia×hybrida* cultivar Titan White, not patented.

*Male parent.*—Unnamed selection of *Petunia×hybrida,* not patented.

Propagation:

*Type cutting.*—Terminal vegetative cuttings.

*Time to initiate roots, summer and winter.*—About 15 days at 20 to 22° C.

*Time to develop roots, summer and winter.*—About 20 days at 18 to 20° C.

*Root description.*—Fine; white, close to 155D, in color.

*Rooting habit.*—Freely branching.

Plant description:

*Form.*—Annual flowering plant; indeterminate; initially upright, then semi-upright to outwardly spreading and cascading; uniformly mounded plant form. Freely branching habit with about 12 lateral branches and numerous secondary lateral branches per plant. Pinching enhances development of lateral branches.

*Usage.*—Appropriate for hanging baskets, window boxes, patio containers and landscape applications.

*Plant height.*—About 13 cm.

*Plant diameter* (*area of spread*).—About 56 cm.

*Vigor.*—Vigorous; moderately rapid growth rate.

*Lateral branches.*—Length: About 28 cm. Diameter: About 5 mm. Internode length: About 1.6 cm. Texture: Pubescent. Color: 145A.

*Foliage description.*—Arrangement: Alternate before flowering; opposite after flowers develop; simple. Length: About 7.1 cm. Width: About 3.8 cm. Shape: Elliptic. Apex: Broadly acute. Base: Attenuate. Margin: Entire. Texture, upper and lower surfaces: Pubescent; glandular; viscid. Venation pattern: Pinnate, arcuate. Color: Developing and fully expanded leaves, upper surface: 146A. Developing and fully expanded fully expanded leaves, lower surface: 146B. Venation, upper and lower surfaces: 147C. Petiole length: About 1.3 cm. Petiole diameter: About 6 mm. Petiole texture, upper and lower surfaces: Pubescent; viscid. Petiole color: 144B.

Flower Description:

*Flower type and habit.*—Single salverform flowers; flowers face mostly upward or outward; axillary. Freely flowering habit, about eight flower buds and open flowers per lateral branch.

*Natural flowering season.*—Long day responsive; long flowering period, spring until frost in the autumn; flowering continuous during this period. Plants start flowering about four to six weeks after planting rooted cuttings. Flowers persistent.

*Flower longevity on the plant.*—About three to five days.

*Fragrance.*—Strong; sweet, vanilla-like.

*Flower size.*—Diameter: Large, about 9.3 cm. Tube length: About 4.5 cm. Throat diameter, distal end: About 2 cm. Tube diameter, proximal end: About 4 mm.

*Flower buds.*—Length: About 4.5 cm. Diameter: About 1.8 cm. Shape: Elongated oblong with flared and ruffled apices. Color: 145C.

*Petals.*—Quantity/arrangement: About five petals fused in a single whorl, funnelform. Length from throat: About 4.5 cm. Width: About 5.3 cm. Shape: Roughly fan-shaped to obovate. Apex: Rounded. Margin: Entire, slightly serrate; ruffled. Texture, upper and lower surfaces: Smooth, satiny. Color: When opening, upper surface: 155A. When opening, lower surface: 145C. Fully opened, upper surface: 155D. Fully opened, lower surface: 157D. Flower throat (inside): 145A to 145B. Flower tube (outside): 145D. Venation, upper petal surface: 145A. Venation, lower petal surface: 145B. Venation, throat: 145A. Venation, tube: 145B.

*Sepals.*—Arrangement/appearance: Single whorl of five sepals fused at base, star-shaped. Length: About 2.5 cm. Width: About 7 mm. Shape: Linear. Apex: Rounded. Margin: Entire. Texture, upper and lower surfaces: Pubescent. Color, upper surface: 147A. Color, lower surface: 147B.

*Peduncles.*—Length: About 3 cm. Width: About 1.5 cm. Angle: About 45° from the stem. Strength: Strong. Texture: Pubescent. Color: 144A.

*Reproductive organs.*—Stamens: Quantity per flower: Five. Anther shape: Ovoid. Anther size: About 2 mm by 3 mm. Anther color: 155A. Pollen amount: Moderate. Pollen color: 160D. Pistils: Quantity per flower: One. Pistil length: About 2.2 cm. Style length: About 1.7 cm. Style color: 145D. Stigma shape: Rounded. Stigma color: 144A. Ovary color: 145B.

*Seed/fruit.*—Seed and/or fruit production has not been observed.

Disease/pest resistance: Plants of the new *Petunia* have not been noted to be resistant to pathogens or pests common to *Petunia*.

Garden performance: Plants of the new *Petunia* have been observed to have good garden performance. Plants of the new *Petunia* have been noted to tolerate temperatures from 0 to 38° C. and have excellent tolerance to rain and wind.

It is claimed:

1. A new and distinct cultivar of *Petunia* plant named 'USTUNI164', as illustrated and described.

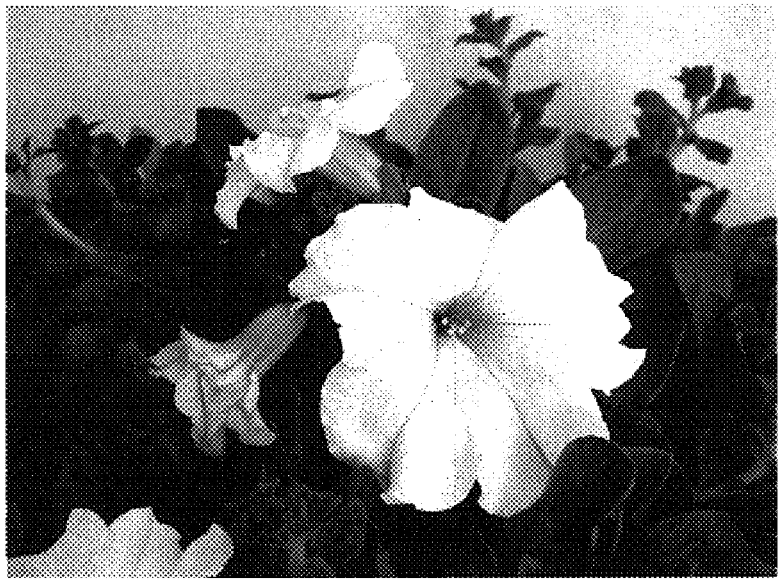
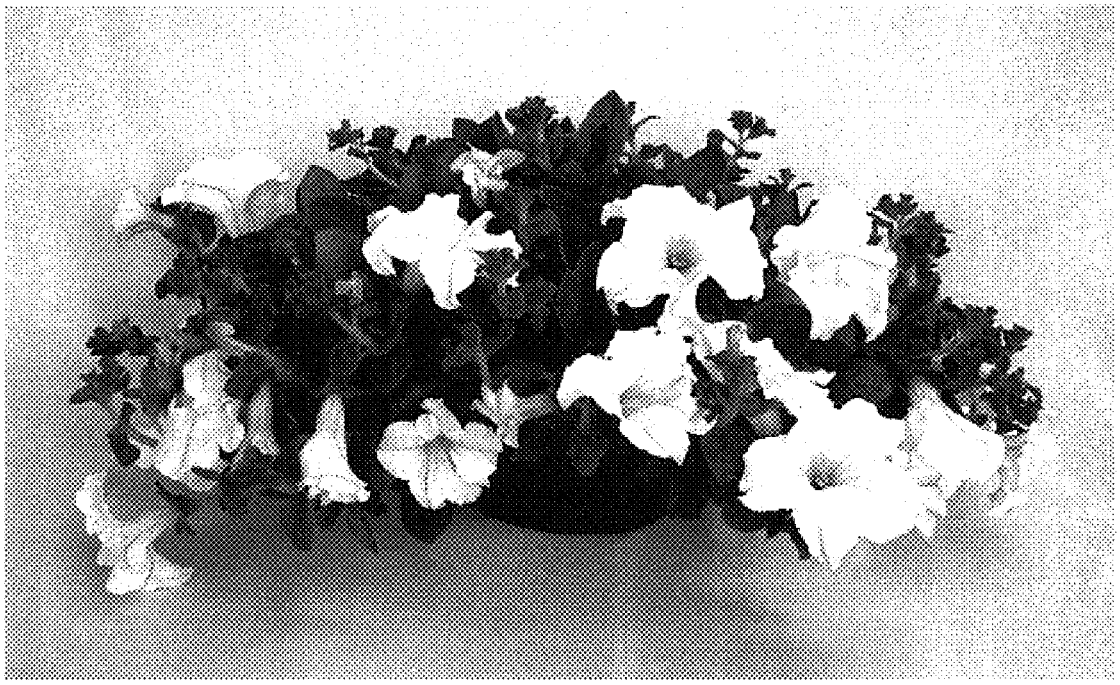

* * * * *